(12) United States Patent
Hess (10) Patent No.: US 10,299,681 B2
(45) Date of Patent: May 28, 2019

(54) IMPLANTABLE MEDICAL DEVICE SYSTEM WITH LEAD CONDUCTOR ANTENNA AND FILTER

(71) Applicant: BIOTRONIK SE & Co. KG, Berlin (DE)

(72) Inventor: James W. Hess, Aloha, OR (US)

(73) Assignee: Biotronik SE & Co. KG, Berlin (DE)

( * ) Notice: Subject to any disclaimer, the term of this patent is extended or adjusted under 35 U.S.C. 154(b) by 6 days.

(21) Appl. No.: 15/650,018

(22) Filed: Jul. 14, 2017

(65) Prior Publication Data

US 2018/0020919 A1    Jan. 25, 2018

Related U.S. Application Data

(60) Provisional application No. 62/364,336, filed on Jul. 20, 2016.

(51) Int. Cl.
*A61B 5/0428* (2006.01)
*A61B 5/00* (2006.01)
*A61B 5/02* (2006.01)
*A61N 1/18* (2006.01)
*A61N 1/37* (2006.01)
*A61N 1/372* (2006.01)
*A61N 1/08* (2006.01)
*A61N 1/05* (2006.01)

(52) U.S. Cl.
CPC .............. *A61B 5/0031* (2013.01); *A61B 5/02* (2013.01); *A61N 1/086* (2017.08); *A61N 1/18* (2013.01); *A61N 1/37* (2013.01); *A61N 1/3718* (2013.01); *A61N 1/37229* (2013.01); *A61N 1/056* (2013.01)

(58) Field of Classification Search
None
See application file for complete search history.

(56) References Cited

U.S. PATENT DOCUMENTS

| | | | |
|---|---|---|---|
| 6,379,300 B1 | 4/2002 | Haubrich | |
| 6,450,172 B1 * | 9/2002 | Hartlaub | A61N 1/37217 128/899 |
| 9,895,534 B2 * | 2/2018 | Stevenson | A61N 1/3754 |
| 2002/0065539 A1 | 5/2002 | Von Arx et al. | |
| 2012/0071956 A1 | 3/2012 | Stevenson et al. | |
| 2013/0073020 A1 | 3/2013 | Mouchawar et al. | |

OTHER PUBLICATIONS

European Search Report for Application No. EP17181652.3 dated Dec. 20, 2017 (English Language).

* cited by examiner

*Primary Examiner* — Kennedy Schaetzle
(74) *Attorney, Agent, or Firm* — Muncy, Geissler, Olds & Lowe, P.C.

(57) ABSTRACT

The invention relates to an implantable medical device system comprising an active medical device having or connected to at least one electrode and circuitry connected to the electrode. The active medical device comprises a telemetry unit. The circuitry connected to the electrode comprises at least one single conductor that provides a radio frequency antenna for the telemetry unit. The implantable medical device system further comprises at least one electronic filter that is arranged between the single conductor of circuitry connected to the electrode and the telemetry unit. The least one electronic filter comprises at least one inductor having a core that comprises a ferromagnetic material with saturating behavior when exposed to an external magnetic field.

15 Claims, 9 Drawing Sheets

IMPLANTABLE MEDICAL DEVICE SYSTEM WITH LEAD CONDUCTOR ANTENNA AND FILTER

This nonprovisional application claims priority to U.S. Provisional Application No. 62/364,336, which was filed on Jul. 20, 2016, and which is herein incorporated by reference.

BACKGROUND OF THE INVENTION

Field of the Invention

The present invention relates to an implantable medical device system including an active medical device with radio frequency (RF) communications capability.

Description of the Background Art

Active medical devices include, for example, implantable monitoring devices such as implantable loop recorders or stimulation devices, such as neurostimulators, pacemakers, biomonitoring devices and the like. Further, many of the devices comprise a telemetry unit for wireless bidirectional data communication to and from the active medical device.

One typical example for an active medical device is an implantable cardiac loop recorder. Existing loop recorders have a sealed housing usually made from titanium. The housing holds the battery and electronic components including a telemetry unit. Typically, the loop recorder includes electrical electrodes for sensing electrical potentials. For instance, such a sensing electrode may be coupled to the housing via a silicon rubber lead which is attached to the housing. The silicon rubber lead includes an electrical conductor that connects the sensing electrode to the loop recorder. An antenna for the telemetry unit may be placed in the lead.

It is possible to use the electrode conductor as the antenna as well as the connection between the electrode and the electronics inside the housing. The advantage of such approach is that existing conductors can be used as an antenna for communication purposes of the telemetry unit and therefore reducing the cost of the lead over an approach using separate antenna and electrode conductors.

Another typical active medical device is an implantable pulse generator, such as an implantable pacemaker. Prior art implantable pacemakers have a sealed housing usually made from metal. The housing houses the battery and further electric and electronic components that for instance include a telemetry unit. Attached to the housing can be a header that comprises electrical connectors for connecting an electric stimulation- and/or sensing lead to the pacemaker. Further, an antenna for the telemetry unit may be placed in the header. The header may be made from plastic material, wherein the electric components of the header, such as contacts and for instance a telemetry antenna, are placed.

The electric lead typically comprises elongated electric conductors. The lead may comprise one or more conductors. The conductors are used to provide an electric connection between electrodes placed in or on the electric lead and electric contacts of a lead connector that is provided to connect the electric lead with the implantable pulse generator. Typically, the contacts are arranged at the proximal end of the electric lead and are configured to match corresponding contacts of the implantable pulse generator. These corresponding contacts usually are placed in the header.

It is possible to use one or more of the electric conductors of the electric lead as (part of) an antenna for the telemetry circuit of the active medical device. In such case, typically electric filters are needed that pass radiofrequency signals to the telemetry unit while blocking lower frequency signals from reaching the telemetry unit. The advantage of such approach is that existing conductors can be used as an antenna for communication purposes of the telemetry unit and therefore no additional hardware has to be added.

While such approach is generally beneficial, it still suffers from the drawback of susceptibility of the active medical device to electromagnetic radiation, such as the magnetic field being exposed to when undergoing a Magnetic Resonance Imaging (MRI) examination. MRI machines generate 3 different fields, a static magnetic field, an electromagnetic RF field, and a gradient magnetic field. The strong static field amounts to typically 1.5 Tesla or 3.0 Tesla, depending on the machine. The RF field has a frequency of typically 64 MHz or 128 MHz depending on the specific MRI machine, wherein the magnetic field component of the electromagnetic RF field is utilized for the imaging process. The gradient field is not relevant to this description. The electronic components of an RF circuit are often sensitive to high voltages. In some cases, an applied voltage of 5V can cause malfunction or damage of the telemetry unit.

The exposure to the fields of an MRI can lead to damage or malfunction of the active medical device. This especially applies to the radio frequency circuit of the telemetry unit, which—when exposed to an MRI field—can be subject to input voltages of 120 Volts or greater.

SUMMARY OF THE INVENTION

It is therefore an object of the invention to provide an improved implantable medical device system.

According to an exemplary embodiment of the invention, this object is achieved by an implantable medical device system comprising an active medical device having or connected to at least one electrode and circuitry connected to the electrode. The active medical device comprises a telemetry unit, wherein the circuitry connected to the electrode comprises at least one single conductor that provides a radio frequency antenna for the telemetry unit (TEL). The implantable medical device system further comprises at least one electronic filter that is arranged between the single conductor of circuitry connected to the electrode and the telemetry unit. The at least one electronic filter comprises at least one inductor having a core or a bead that comprises a ferromagnetic material with saturating behavior when exposed to an external magnetic field.

According to an embodiment of the invention, the core can have a shape of a bead or a toroid made of ferrite or a Mu-metal or a combination of both, wherein the bead or toroid can be constructed in a way that it surrounds the inductor or wraps around the wire of the inductor. In an aspect of the invention, the inductor and the core can be implemented as toroidal inductor, i.e. the core and the wire of the inductor are constructed wrapped around each other and have in total a toroidal shape.

The term 'core' can be understood as a part made of the material having a geometrical shape which is suitable for usage as inductor core, e.g. a cuboid, a cube or the like. Moreover, the term 'core' can also be used as equivalent to a bead made of the material.

Inductors can be created by winding turns of wire around a core. The inductance of the inductor is determined by its geometry, the number of turns around the core and the magnetic permeability of the core material.

The invention includes the aspect that in the context of active medical devices, the characteristics of a ferromagnetic inductor core can be systematically utilized in order to decrease the susceptibility of the active medical device to electromagnetic radiation. This aspect is in opposition to the usual application of inductors, where such described saturation is sought to be avoided.

According to an embodiment of the invention, the electronic filter of the implantable medical device system is at least one of, or a combination of a high pass filter, low pass filter or a band pass filter.

In an embodiment of the implantable medical device system according to the invention, the electronic filter of the implantable medical device system can be arranged and configured to provide low attenuation of electromagnetic fields when the inductor core is not saturated and can provide high attenuation of electromagnetic fields when the inductor core is saturated.

According to an embodiment of the present invention, the low attenuation is provided for RF magnetic or electromagnetic fields in a first frequency range and the high attenuation is provided for RF magnetic or electromagnetic fields in a second frequency range.

According to an embodiment of the present invention, the first frequency range has a lower limit of approximately 400 MHz. For example, the first frequency range encompasses a frequency subrange from 401 MHz to 457 MHz.

In an embodiment of the present invention, the second frequency range can encompass at least a frequency of 128 MHz and/or at least one other frequency associated with the high frequency magnetic field of an MRI machine and/or a frequency range from range from 120 MHz to 136 MHz and/or a frequency range from 50 MHz to 150 MHz and/or a frequency range from 60 MHz to 68 MHz.

According to an embodiment of the present invention, the level of the low attenuation of the electronic filter can be below 20 dB and/or the level of high attenuation of the electronic filter can be in a range of 20 dB or more.

In an embodiment of the present invention, the electronic filter can be a one pole filter or a multi pole filter.

According to an embodiment of the present invention, ferromagnetic material of the core of the inductor can be a ferrite or a Mu-metal or a combination of both.

Ferrite and Mu-metal have very high relative permeability and can be as high as 20,000. These core materials also exhibit a property called saturation. When exposed to a high magnetic field, its permeability drops to close to that of free space. Thus a mu-metal that has a relative permeability of 20000 under low magnetic field conditions will have a relative permeability of close to 1 under high magnetic field conditions. An inductor with a core made of this material, having an inductance of 20000 nH under low field conditions, would have an inductance of close to 1 nH when the core is saturated. Moreover, other ferromagnetic materials which are applicable for the purpose according to the invention can be considered for the core material.

In an embodiment of the present invention, the core of the inductor can be configured to saturate in a magnetic field with a magnetic flux density that amounts to a value between 1 mT and at least 150 mT, alternatively between 1 mT and 3 T, 1 mT and 4 T or between 1 mT and 7 T.

According to an embodiment of the present invention, a radio frequency antenna can be adapted for wireless communication in a frequency range from 401 MHZ to 457 MHz, in particular according to the Medical Implant Communication Service specification and/or the Medical Device Radiocommunications Service specification.

In an embodiment of the present invention, the implantable medical device system can be connected to an implantable lead, wherein the electronic filter can be located in the proximal end of the implantable lead.

According to an embodiment of the present invention, an active medical device for an implantable medical device system according to an embodiment of the invention is provided. The active medical device has an input that is connected or can be connected to an electrode or circuitry connected to an electrode or an implantable lead. The active medical device comprises a telemetry unit, wherein the electronic filter is arranged between the input for the electrode or the circuitry connected to the electrode or the implantable lead and/or the telemetry unit.

According to a further aspect of the invention, an implantable lead for an implantable medical device system is proposed. The implantable lead comprises a lead body and a lead connector that can be arranged at a proximal end of the lead body, wherein the electronic filter can be arranged within the lead body close to the proximal end of the implantable lead or within the lead connector.

According to the invention and the presented embodiments and aspects, the susceptibility of an active medical device to electromagnetic radiation is decreased significantly in order to enable the patient to be safely exposed to electromagnetic fields, particularly when being examined in a MRI system, without any harm to the patient and the active medical device.

In an exemplary embodiment of the present invention, the implantable medical device comprises a LC high pass filter which is constructed with using a 30 pF capacitor and a 10 nH inductor, wherein the inductor has a ferromagnetic core made with a material with a relative permeability of 1000. In normal operation, this filter has a corner frequency of approximately 300 MHz. It passes 400 MHz telecommunication signals to and from the telemetry unit as designed. Under these conditions, the filter attenuates signals at 128 MHz (an MRI RF field frequency) by about 12 dB. Thus an electrical signal of 120V and 128 MHz would result in a signal of about 30V being imposed on the downstream RF electronics. Since they may not be able to withstand voltage above 2.5 V, they would possibly be damaged by this signal. However, when the implantable medical device is brought close to an MRI machine, the large static magnetic field saturates the core of the inductor used in the high pass filter. This changes the frequency response of the filter, resulting in an attenuation at 128 MHz of close to 70 dB instead of an attenuation of 12 dB. Now, when the MRI's RF field imposes a voltage of 120V on the device, the filter attenuates the voltage to 0.025V, which will not damage the electronics. Thus the electronics are protected from the RF field of the MRI machine by this invention. The further away from the isocenter of the MRI machine, the weaker both the RF and the static fields become.

Preferably, the core of the inductor saturates below the 1.5 T or 3.0 T magnetic field flux densities of the machines. In an embodiment of the present invention, the inductor core saturates at less than 100 mT.

According to an embodiment of the invention, an implantable medical device system is disclosed which comprises an active medical device that is connected to an implantable lead. The active medical device comprises a telemetry unit. The implantable lead comprises at least one single conductor that provides a radio frequency antenna for the telemetry unit. The implantable medical device system further comprises at least one LC high pass filter that is arranged between the single conductor of implantable lead and the telemetry unit. The LC high pass filter comprises at least one capacitor and at least one inductor. The inductor has a core that comprises a ferromagnetic material with saturating behavior when exposed to an external magnetic field. The LC high pass filter is arranged and configured to provide a pass-band above 400 MHz when the core is not saturated and to increase its attenuation from a low attenuation level to a high attenuation level when exposed to an external magnetic field.

Thus, when the inductor core is not exposed to a magnetic field and therefore not saturated, the corresponding inductor features a high inductivity. Vice versa, when exposed to a magnetic field, the inductor core saturates, therefore lowering the inductor's inductivity. That is, because the inductor's inductivity L depends—besides on the inductor's number of windings N, its length l and cross-sectional area A—on the core's permeability $\mu_r$.

The core's permeability $\mu_r$ describes the relation between magnetic flux density B and the magnetic field strength H. In contrast to diamagnetic materials (e.g. nitrogen, copper) and paramagnetic materials (e.g. oxygen, air), which feature a linear permeability $\mu_r$, ferromagnetic materials feature a permeability $\mu_r$ that is characterized by a degressive curve. Hence, the exposure to a magnetic field leads to a sudden saturation of a ferromagnetic core of the inductor, significantly lowering the inductor's inductivity L and causing the inductor to function as an air core part.

As opposed to the usual application of inductors, where such described saturation is sought to be avoided, the invention includes the recognition that in the context of active medical devices, the characteristics of a ferromagnetic inductor core can be systematically utilized in order to decrease the susceptibility of the active medical device to electromagnetic radiation. That is, because the reduction of the inductor's inductance of the LC high pass filter leads to an attenuation of the characteristic MRI frequencies between 100 MHz and 200 MHz, particularly between 120 MHz and 130 MHz, that otherwise would have disturbed the active medical device, in, for example, the telemetry unit.

In such system, the susceptibility of the active medical device to electromagnetic radiation is decreased significantly in order to enable the patient to be safely exposed to electromagnetic fields, particularly when being examined in a MRI system, without any harm to the patient and the active medical device. This particularly applies for active medical devices with integrated antennas. Accordingly, the invention provides a means for protecting the device, particularly the telemetry unit, from excess voltages that are induced through the electric lead during MRI examinations, while maintaining the filter function for passing the radiofrequency signals to the telemetry unit under normal operating conditions.

The invention further includes the recognition that other ways of achieving this object, such as a magnetic sensor together with a switch to disconnect the antenna from the circuit when an MRI field is present, would imply a significant increase of cost and device complexity, as switching and sensing components have to be added to the device. Also other measures such as applying multistage or higher order filters with additional poles to obtain a sharper cutoff between the frequencies of interest would lead to similar problems as they require additional components and lead to additional attenuation in the radio frequency band. Lastly, the deployment of diode clamps would also require additional components and cost. They would also introduce capacitance into the circuit that would complicate the radio frequency design. Therefore, in contrast to all of these approaches, the application of an LC high pass filter according to the invention achieves the abovementioned object while keeping cost and device complexity low.

In an embodiment of the implantable medical device system, the LC high-pass filter is a two-pole filter. Concretely, such two-pole filter may be comprised of one capacitor and one inductor. A main advantage of a two-pole filter as opposed to filters with a higher number of poles is that only requires a relatively small amount of hardware components for its realization. Furthermore, the attenuation within the radio frequency band is smaller than with filters with a higher number of poles.

In an embodiment of the invention, the ferromagnetic material is Ferrite. This particularly leads to the saturating behavior of the inductor when being exposed to an electromagnetic field. Through this, the above described advantage of an adaptive attenuation behavior of the LC high pass filter is achieved. For example, the ferromagnetic material can be a Mu-metal.

The LC high pass filter can be configured to provide an increase of the attenuation of at least 20 dB at frequencies between 100 MHz and 200 MHz when exposed to an external magnetic field. This leads to the beneficial attenuation characteristics regarding the electromagnetic fields generated by a MRI device, which normally feature a frequency of approximately 124 MHz.

In an embodiment, the core of the inductor can be configured to saturate in a magnetic field with a magnetic flux density that amounts to a value between 1 T and 4 T. This also leads to the beneficial attenuation characteristics regarding the static fields generated by a MRI device, which normally feature magnetic flux densities of around 3 T.

The core of the inductor can be configured to saturate in a magnetic field with a frequency in the range between 120 MHz and 130 MHz. This leads to the advantage, that the beneficial attenuation characteristics are achieved independent of the design of the inductor and particularly the inductor core.

The increase of the attenuation of the LC high pass filter caused by the saturation of the inductor core leads to a decrease of the signal amplitude at a frequency between for instance 100 MHz and 200 Mhz that amounts to a value between 15 dB and 20 dB. This implies that during normal operation of the pacemaker, the LC high pass filter features a behavior that lets signals having a frequency of, for instance, more than 400 MHz pass to the telemetry unit, but attenuates frequencies below the radio frequency range used for telemetry.

In an embodiment, the high attenuation level of the LC high pass filter can amount to a value, for example, between 55 dB and 65 dB. This implies that during an exposure to an electromagnetic field, e.g. generated by a MRI device, the attenuation behavior of the LC high pass filter is altered in a beneficial way. Particularly, the increased attenuation of frequencies of the electromagnetic fields generated by MRI devices leads to a high robustness of the pacemaker against MRI radiation.

In an embodiment, the radio frequency antenna can be adapted for wireless communication in a frequency range between 401 MHZ and 457 MHz, in particular according to the Medical Implant Communication Service specification and/or the Medical Device Radio-communications Service specification. This leads to the advantage that the active medical devices accounts for frequencies that are most likely to be used in medical device radio communication. More specifically, the invention can account for the Medical Implant Communication Service specification (MICS) of the European Telecommunications Standards Institute (ETSI), that uses a frequency range between 401 MHz and 406 MHz. The invention furthermore accounts for the Medical Device Radiocommunications Service specification (MedRadio) of the U.S. Federal Communications Commission (FCC), that uses several frequency ranges between 401 MHz and 457 MHz.

The LC high pass filter can be located in the proximal end of the implantable lead. The arrangement of the LC high pass filter within the implantable lead has the advantage of increased modularity, as the high pass filter function according to the invention could be implemented outside and therefore independently of the pacemaker housing.

In an embodiment, the active medical device can have an input that is connected or can be connected to an implantable lead and comprises a telemetry unit, wherein the LC high pass filter can be arranged between the input for the implantable lead and the telemetry unit. Such arrangement of the LC high pass filter has the advantage of a better integration, as the LC high pass filter can be placed within the existing housing not subject to strict space constraints (compared to an integration of the LC high pass filter into the proximal end of the lead) and close to the circuitry to be attached to.

The invention also provides an implantable lead for an implantable medical device system. The implantable lead comprises a lead body and lead connector that can be arranged at a proximal end of the lead body, wherein the LC high pass filter can be arranged within the lead body close to the proximal end of the implantable lead or within the lead connector.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
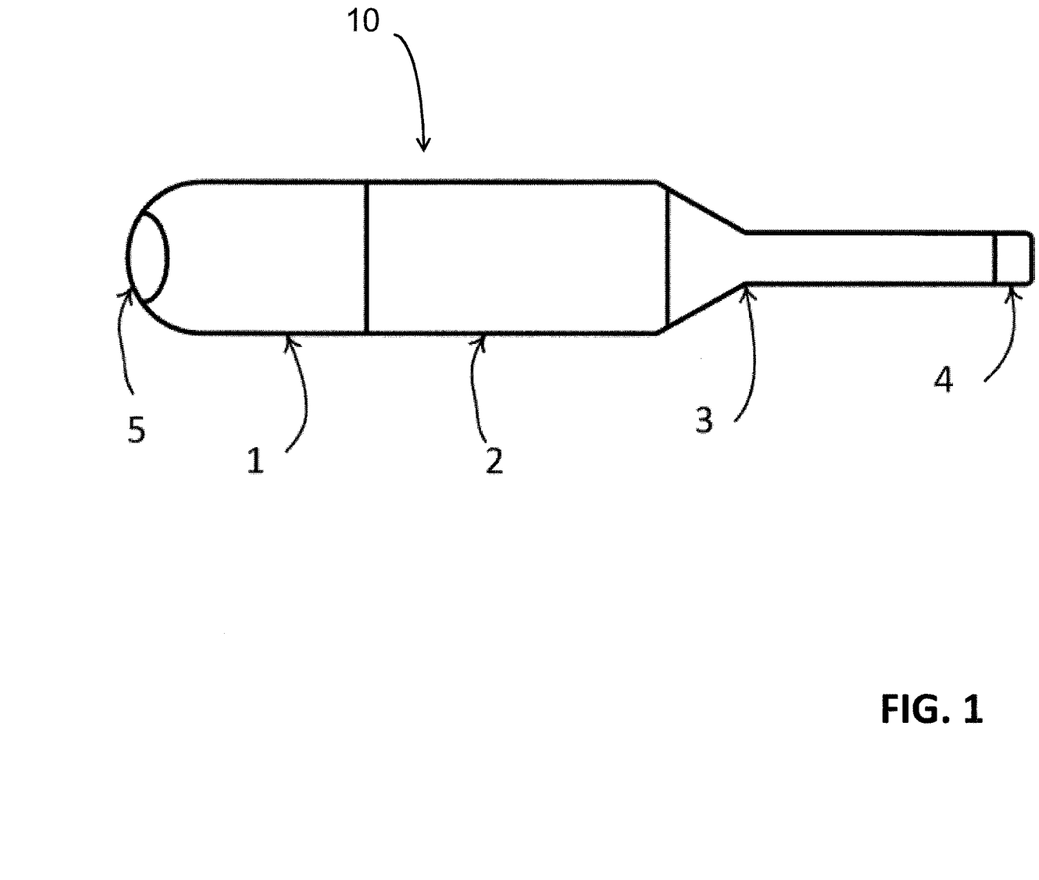
FIG. 1 shows an active medical device with a permanently attached lead.

In FIG. 1, an implantable loop recorder 10 with typical components is shown. A battery 1 is connected to the housing 2. The lead 3 connects the housing 2 to the electrode 4. The lead contains the electrical conductor which connects electrode 4 with the implant circuitry within housing 2. The conductor may have a coating made of electrical insulating material, such as silicone. Typically, implantable loop recorder 10 is manufactured as one unit, meaning that lead 3 is not interchangeable. A second electrode 5 is on the exterior of the battery 1.

Figure 2:
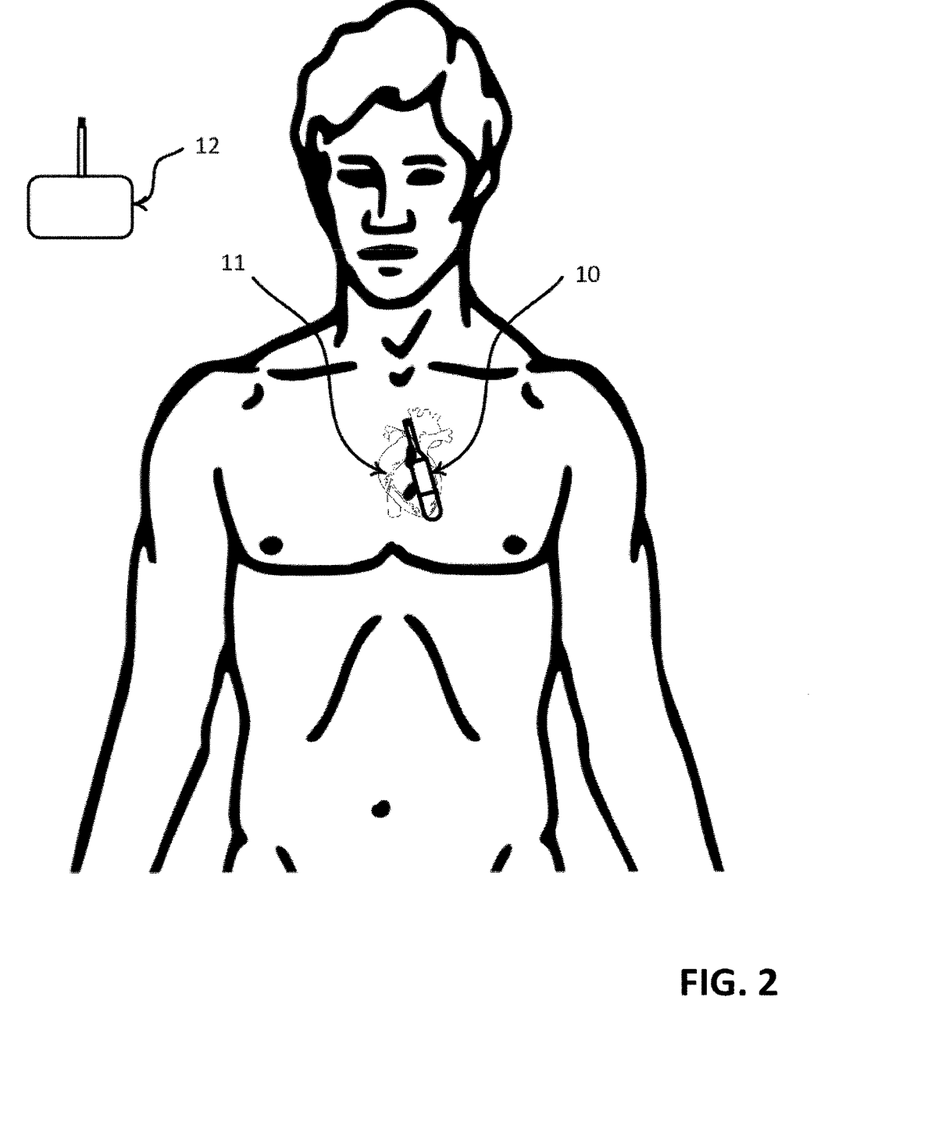
FIG. 2 shows schematically an active medical cardiac monitor which is implanted in a patient. Furthermore, an external RF transceiver is shown which communicates with the implant.

In FIG. 2, the implantable loop recorder 10 is shown in a typical implant location in the chest of a patient over the heart 11. Electrical fields generated by the patient's heart during a beat create a voltage differential between the two electrodes 4 and 5. This voltage is recorded by the implantable loop recorder. These signals are recorded, and the later transmitted to an external receiver 12.

Figure 3:
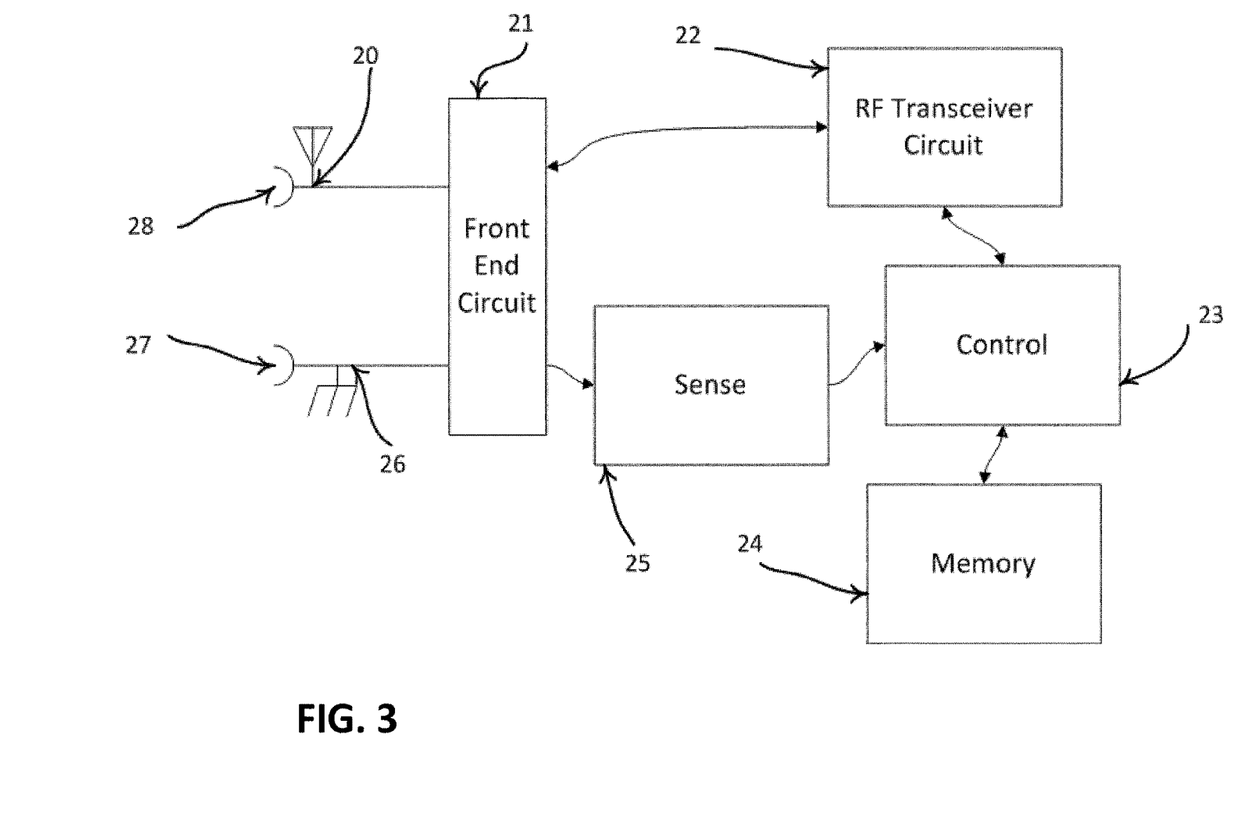
FIG. 3 shows a schematic block diagram of some components of the active medical device.

FIG. 3 is a simplified block diagram of an implantable loop recorder 10. When the patient's heart beats and generates an electric field, that field causes a voltage to appear across the electrodes 4 and 5, represented via the terminals 27 and 28, while 26 is the ground reference. The voltage is separated from the RF signal in the front end circuitry 21 and directed to sense block 25. In the sense block 25, the signal is further processed and converted to a digital signal. Control block 23 records this signal for later recall in the memory 24. At appropriate intervals, control block 23 reads the recorded heart signal from the memory 24 and, using the RF transceiver circuit 22 transmits the signal to an external receiver. The RF transceiver 22 formats and modulates the signal for transmission and routes this RF signal to the front end circuit 21. The front end circuit routes the RF signal to the antenna 20. During the transmission process, the RF unit 22 may receive handshaking signals from the external unit 12.

Figure 4:
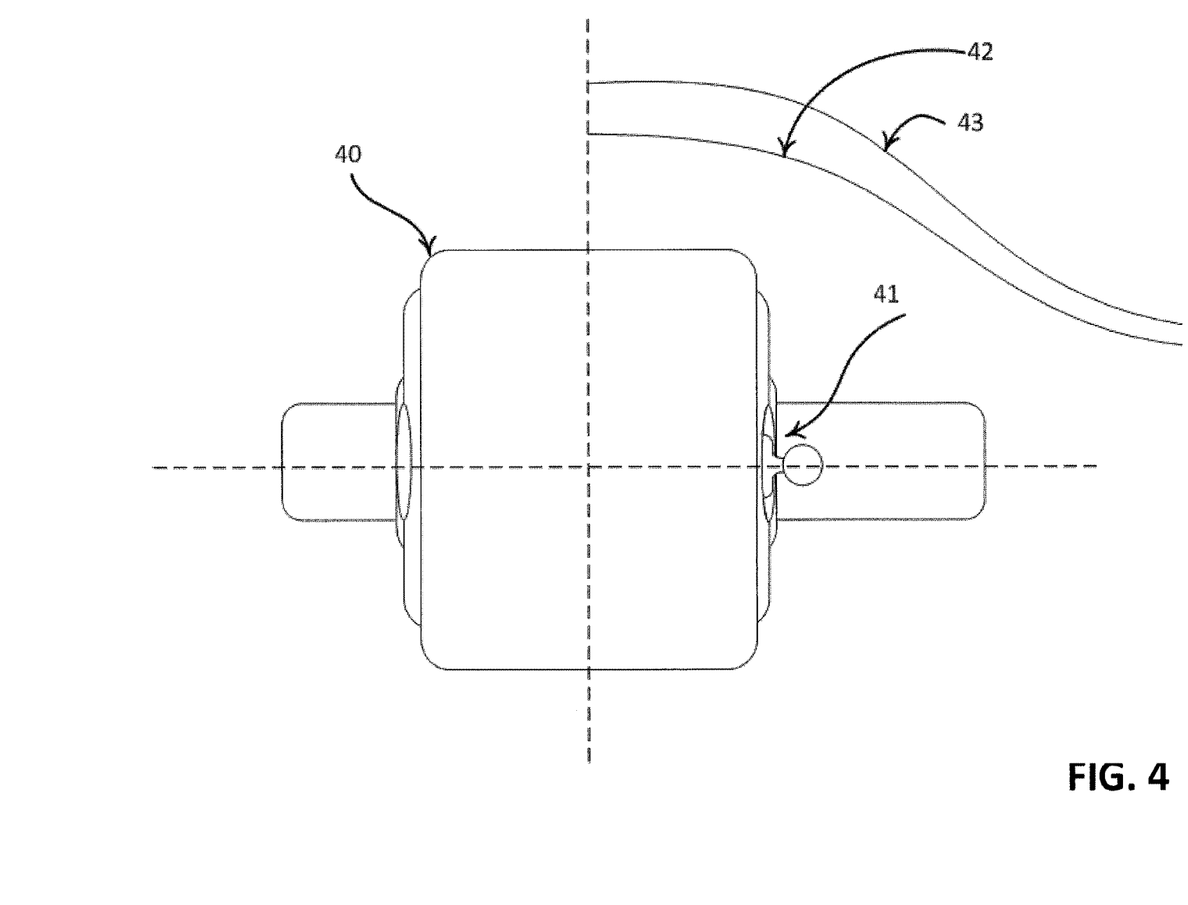
FIG. 4 shows schematically the top view of an MRI machine with a graph illustrating how the static and RF field strengths relate to distance from the machine.

FIG. 4 illustrates a schematic top view of an MRI machine 40 with patient 41. Curve 43 illustrates how the magnitude of the static magnetic field peaks at the isocenter of the MRI machine and falls off as the distance from the isocenter increases. Curve 44 illustrates how the magnitude of the RF magnetic field peaks at the isocenter of the MRI machine and falls off as the distance from the isocenter increases.

Figure 5:
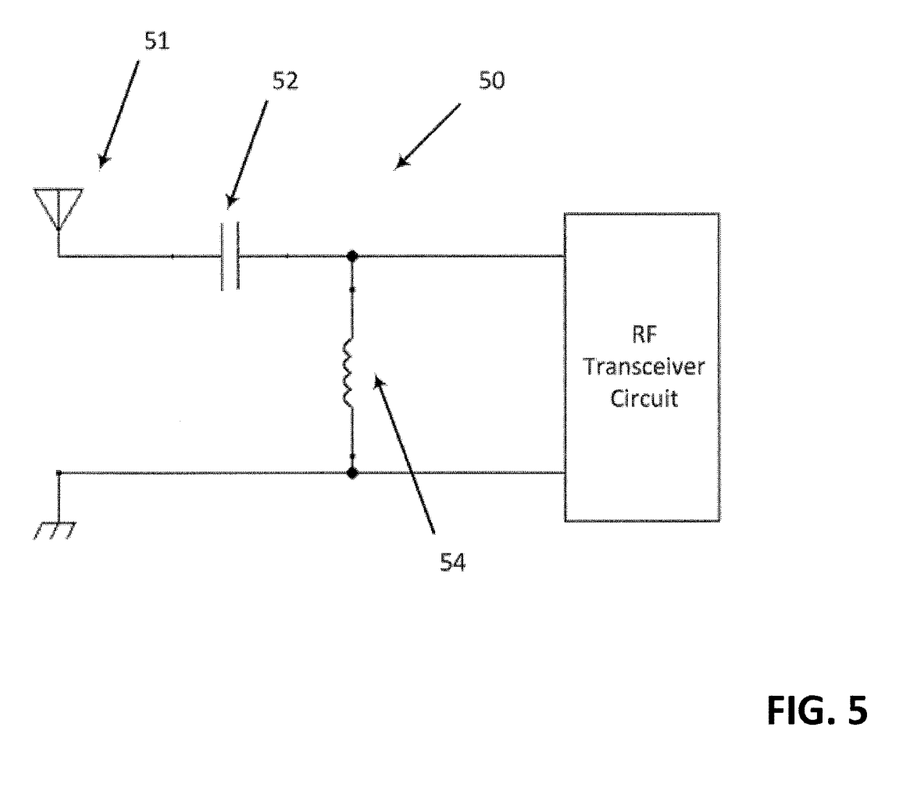
FIG. 5 shows a circuit diagram of a LC high pass filter.

FIG. 5 shows an exemplary circuit diagram of an electronic filter 50 as a simple 2-pole LC high pass filter according to embodiments of the present invention. Capacitor 52 tends to have low impedance at high frequencies and high impedances at low frequencies. Inductor 54 tends to have low impedance at low frequencies and high impedance at high frequencies. These two components work together to create the filter. The characteristics of the filter, particularly the frequency above which the filter passes signals, can be changed by adjusting the values of the inductor and capacitor using the formula fc=1/(2*π*Sqrt(LC)). For example: The illustrated High Pass filter with L=47 nH and C=4 pF will give a corner, or cutoff, frequency of 367 MHz. Assuming inductor 54 has a core which is made from a material with a relative permeability of 1000, when the circuit is close enough to the MRI machine such that the static field causes the inductor core to saturate. The inductor now has a value of 0.047 nH. This gives a corner frequency of 1.1 GHz. More importantly this also results in the attenuation of a signal at 128 MHz to change from −17 dB to −80 dB. Thus when a 122V, 128 MHz RF signal from a 3.0 T MRI machine is applied, the unsaturated filter, the output voltage would be 17V which could damage the circuit. The same input voltage applied to the saturated filter produces only a 15 mV signal on the filter output, which is well within the 2.5V range that the RF electronics can safely tolerate. Referring to FIG. 1, filter 50 can for instance be implemented in connection with the conductor which connects electrode 4 with the implant circuit.

Figure 6:
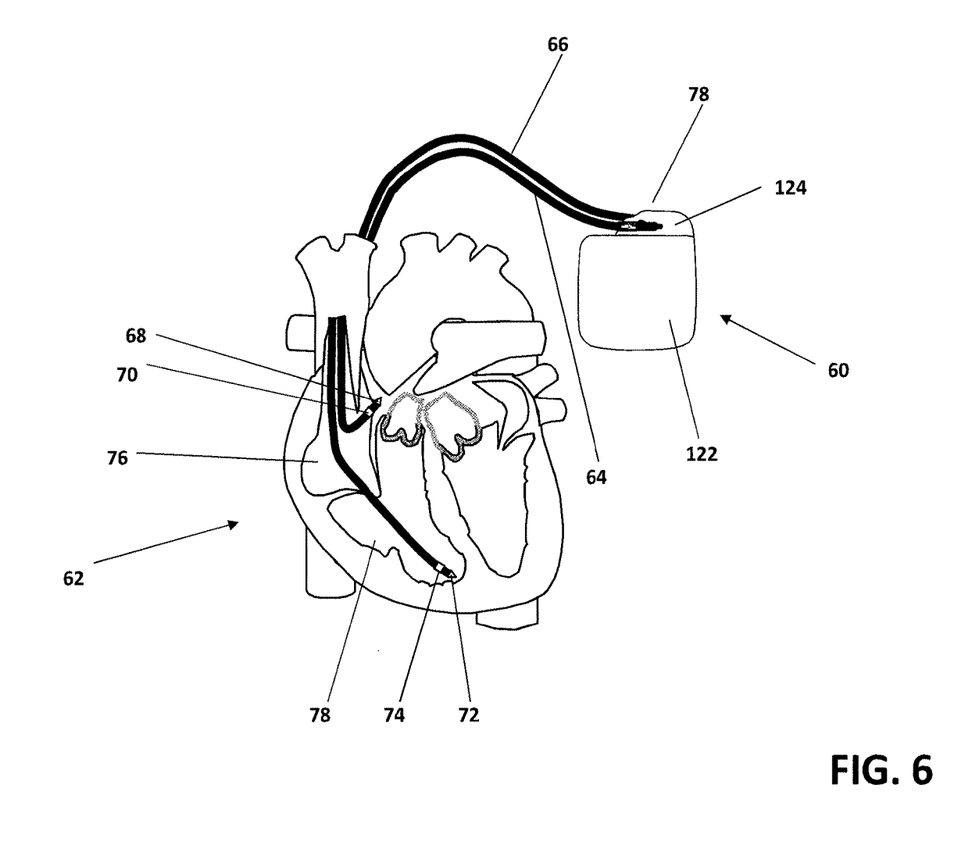
FIG. 6 shows an active medical device and an electric lead connected thereto.

In FIG. 6 an embodiment of the present invention is depicted, where the active medical device is a dual chamber pacemaker 60 as heart stimulator which is connected to pacing/sensing leads placed in a heart 62 is illustrated. The pacemaker 60 is comprised of a housing 122, which houses the battery and further electric and electronic components, that for instance include a telemetry unit 92. The pacemaker 60 is furthermore comprised of a header 124 that comprises electrical connectors for connecting an electric stimulation-and/or sensing lead to the pacemaker.

The pacemaker 60 is electrically coupled to heart 62 by way of leads 64 and 66. Lead 64 has a pair of right atrial electrodes 68 and 70 that are in contact with the right atria 76 of the heart 62. Lead 66 has a pair of electrodes 72 and 74 that are in contact with the right ventricle 78 of heart 62. Electrodes 68 and 72 are tip-electrodes at the very distal end of leads 64 and 66, respectively. Electrode 68 is a right atrial tip electrode RA-Tip and electrode 72 is a right ventricular tip electrode RV-Tip. Electrodes 70 and 74 are ring electrodes in close proximity but electrically isolated from the respective tip electrodes 68 and 72. Electrode 70 forms a right atrial ring electrode RA-Ring and electrode 74 forms a right ventricular ring electrode RV-Ring.

Leads 64 and 66 each comprise elongated electric conductors 80, 80', 80" and 80'" (cf. FIG. 8), each conductor providing an electric connection between the electrodes 68, 70, 72 and 74 and electric contacts of a lead connector that is provided to connect the electric lead with the implantable pulse generator. Typically, the contacts are arranged at the proximal end of the electric lead and are configured to match corresponding contacts of the implantable pulse generator. These corresponding contacts usually are placed in the header 124.

Electrodes of the electric lead are placed at or close to a distal end of the electrode lead. Therefore, one or more electric conductors are running along more or less the entire length of the electric lead. In many cases, the electric lead comprises a helical wire that mechanically stabilizes the electric lead and that can serve as conductor for electrically connecting an electrode to the corresponding lead connector contact of the lead connector.

Figure 7:
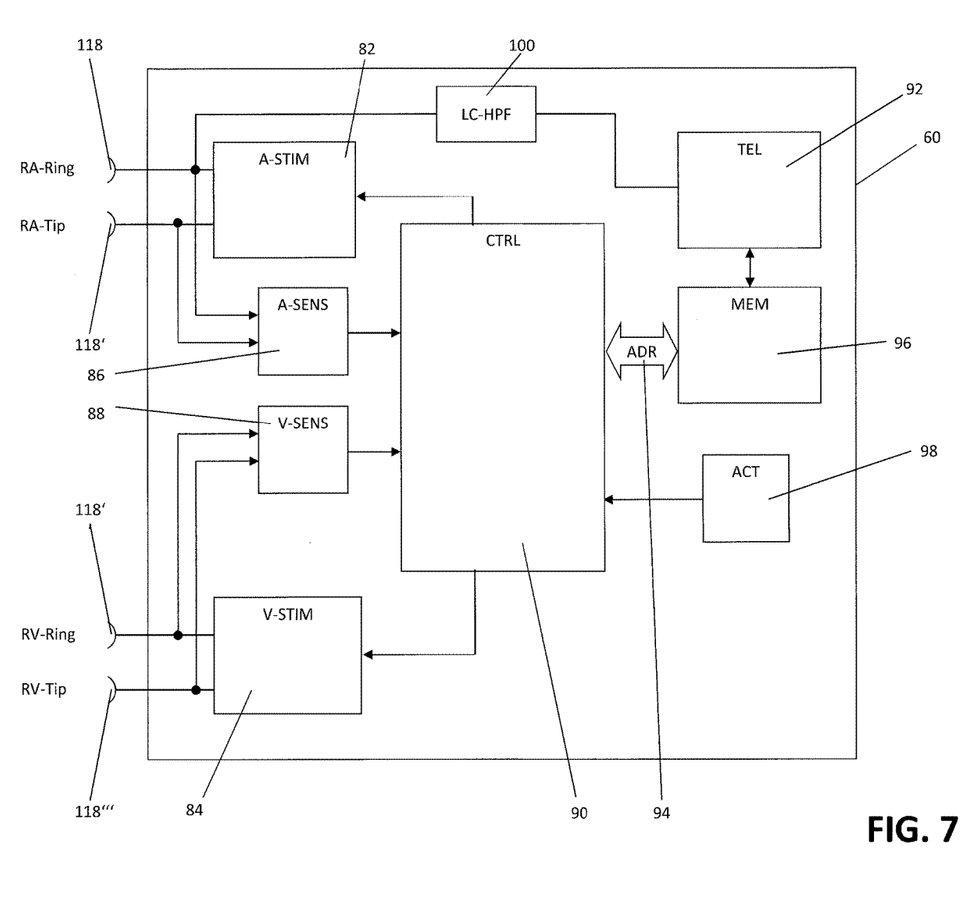
FIG. 7 is a schematic block diagram of some components of an exemplary active medical device (AMD)

Referring to FIG. 7 a simplified block diagram of a dual chamber pacemaker 60 is illustrated. During operation of the pacemaker leads 64 and 66 are connected to respective output/input terminals 118, 118', 118", 118'" of pacemaker 60 as indicated in FIG. 6 and carry stimulating pulses to the tip electrodes 68 and 72 from an atrial stimulation pulse generator A-STIM 82 and a ventricular pulse generator V-STIM 84, respectively. Further, electrical signals from the atrium are carried from the electrode pair 68 and 70, through the lead 64, to the input terminal of an atrial channel sensing stage A-SENS 86; and electrical signals from the ventricles are carried from the electrode pair 72 and 74, through the lead 66, to the input terminal of a ventricular sensing stage V-SENS 88.

Controlling the dual chamber pacer 60 is a control unit CTRL 90 that is connected to sensing stages A-SENS 86 and V-SENS 88 and to stimulation pulse generators A-STIM 82 and V-STIM 84. Control unit CTRL 90 receives the output signals from the atrial sensing stage A-SENS 86 and from the ventricular sensing stage V-SENS 88. The output signals of sensing stages A-SENS 86 and V-SENS 88 are generated each time that a P-wave representing an intrinsic atrial event or an R-wave representing an intrinsic ventricular event, respectively, is sensed within the heart 62. An As-signal is generated, when the atrial sensing stage A-SENS 86 detects a P-wave and a Vs-signal is generated, when the ventricular sensing stage V-SENS 88 detects an R-wave. Control unit CTRL 90 also generates trigger signals that are sent to the atrial stimulation pulse generator A-STIM 82 and the ventricular stimulation pulse generator V-STIM 84, respectively. These trigger signals are generated each time that a stimulation pulse is to be generated by the respective pulse generator A-STIM 82 or V-STIM 84. Control unit CTRL 90 comprises circuitry for timing ventricular and/or atrial stimulation pulses according to an adequate stimulation rate that can be adapted to a patient's hemodynamic need.

Still referring to FIG. 7, the dual chamber pacemaker 60 includes a memory circuit MEM 96 that is coupled to the control unit CTRL 90 over a suitable data/address bus ADR 94. This memory circuit MEM 114 allows certain control parameters, used by the control unit CTRL 90 in controlling the operation of the dual chamber pacemaker 60, to be programmably stored and modified, as required, in order to customize the implantable medical device's operation to suit the needs of a particular patient.

In order to be able to detect periods of physical activity of a patient indicating that the patient is awake and in order to allow rate adaptive pacing, the dual chamber pacemaker 60 further includes a physiological sensor ACT 98 that is connected to the control unit CTRL 90 of the dual chamber pacemaker 60.

Further, a LC high pass filter 100 is arranged between a wire leading to the telemetry unit 92 and a wire that connects to an AMD connector contact 118. The AMD connector contact 118 is one of a plurality of AMD connector contacts 118, 118', 118" and 118'", that corresponds to one lead connector contact 120 of a plurality of lead connector contacts 120, 120', 120" and 120'" comprised in the lead connector 116.

Through the AMD connector contact 118, respectively the lead connector contact 120, the input of the LC high pass filter 100 is galvanically connected to at least a single conductor 80, for example a wire, of the implantable lead 64 that connects to the right atrial ring electrode RA-Ring 70, and also to the atrial stimulation pulse generator 82 as well as to the atrial sensing stage 86. It is one purpose of the AMD connector contact 118 to enable the transmission of signals from the right atrial ring electrode RA-Ring 70 to the atrial sensing stage 86, and vice versa, the transmission of stimulation pulses from the atrial stimulation pulse generator 82 to the right atrial ring electrode RA-Ring 70. Furthermore, it is a purpose of the AMD connector contact 118 to connect the LC high pass filter 100 and ultimately, the telemetry unit 92 to the above mentioned wires in order to enable the telemetry unit 92 to receive and send radio frequency signals, using the wires connected to the AMD connector contact 118, in particular the single conductor 80, as an antenna. The purpose of the LC high pass filter 100 during normal operation is to pass signal frequencies equal to or higher than 400 MHz from the wires connected to the AMD connector contact 118 to the telemetry unit 92, while blocking out frequencies lower than 400 MHz. Analogously, the AMD connector contact 118 could also be connected via another lead connector of the plurality of lead connectors to another electrode, such as the right atrial tip electrode RA-Tip 68 or the right ventricular tip electrode RV-Tip 72 or the right ventricular ring electrode RV-Ring 74. By doing so, either of these wires could be connected to the telemetry unit 92 via the LC high pass filter 100 and then would serve as an antenna for the telemetry unit 92. Also the AMD connector contact 118 could be connected to an electrode of another active medical device, such as a neurostimulator.

The telemetry unit 92 again is connected to the memory circuit 96, allowing for a bidirectional communication. Through this, the telemetry unit 92 can access parameters on the memory circuit 96 that subsequently can be transmitted by the telemetry unit 92 and the wires connected to the AMD connector contact 118 to a suitable wireless communication device via radio transmission. Vice versa, parameters can be transmitted from a suitable wireless communication device via radio transmission to the telemetry unit 92, and ultimately stored in the memory circuit 96.

Figure 8:
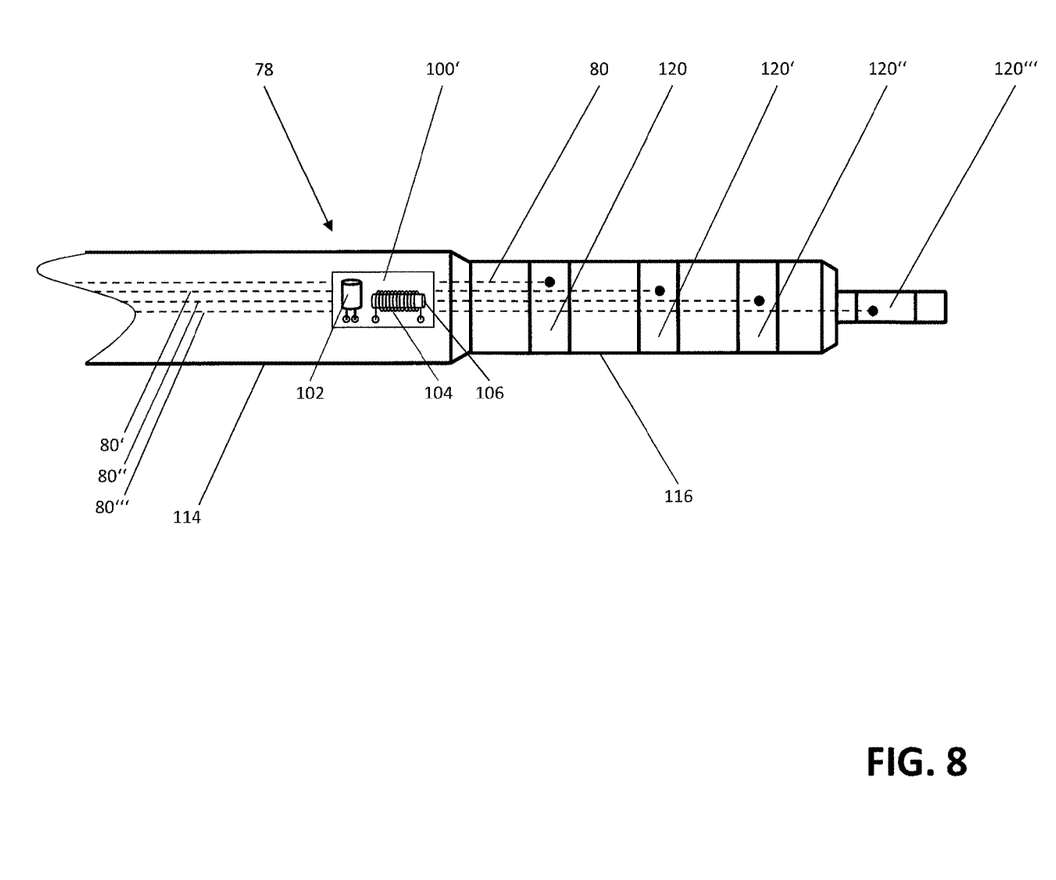
FIG. 8 is a schematic side-elevated view of an electric lead connector.

In FIG. 8 a proximal end portion of an electric lead according to the invention is illustrated. At the proximal end of each lead 64 or 66, al lead connector 116 is arranged and attached to a lead body 114 of lead 64 or 66. The lead connector 116 provides a plurality of lead connector contacts 120, 120', 120" and 120'''. In the lead body 114, a plurality of conductors 80, 80', 80" and 80''' are arranged, each extending from one of the lead connector contacts 120, 120', 120" and 120''' to a respective electrode on the respective electric lead 64 or 66.

A single conductor 80 of the plurality of conductors is galvanically connected to the corresponding lead connector contact 120 of a plurality of lead connector contacts 120, 120', 120" and 120'''.

Of the lead connector contacts, at least some are electrically connected to a respective one of the electrodes at the distal end of the respective electric lead by means of a respective conductor 80, 80', 80" or 80'''. At least one conductor 80 of the plurality of conductors 80, 80', 80" and 80''' is connected to the respective lead connector contact 120 via a LC high pass filter 100' which is an embodiment of the electronic filter 50 according to the invention. Thus, conductor 80 can serve for a double purpose, that is, the conductor serves as an electric connection between e.g. the right atrial ring electrode 70 and a lead connector contact 120 and as an antenna for the telemetry unit 92.

The single conductor 80 can be a wire comprised of a conducting material. e.g. a metal wire. Preferable, conductor 80 is a helically wound wire that further serves to mechanically stabilize electric lead 64. In an alternative embodiment, conductor 80 can be a straight wire.

It is noted, that other conductors can be connected to the respective lead connector contact via an LC high pass filter instead of conductor 80. Likewise, any of the conductors of any lead can be configured to act as antenna for the telemetry unit. However, in an embodiment providing one helically wound wire, it is preferred to use the helically wound wire as the antenna because other conductors that are enclosed by the helically wound wire might be shielded by the helically wound wire.

The LC high pass filter 100' comprises a capacitor 102 and a wire wound inductor 104, wherein the inductor 104 comprises an inductor core 106 of a ferromagnetic material.

Regarding the embodiments of FIG. 7 and FIG. 8, it is noted that it may be sufficient to provide only one LC high pass filter that alters its parameters in an impeding magnetic field, either in the active medical device or in an electric lead to be connected to the active medical device.

Referring to FIG. 1, it is noted that the filter configuration from FIG. 8, comprising capacitor 102 and inductance 104 with inductor core 106 may also be implemented in the lead 3, in particular in connection with the conductor which connects electrode 4 with the implant circuitry. Moreover, it is noted that the application of other forms of electronic filters 50 which are suitable for the purpose according to the invention are possible.

Figure 9:
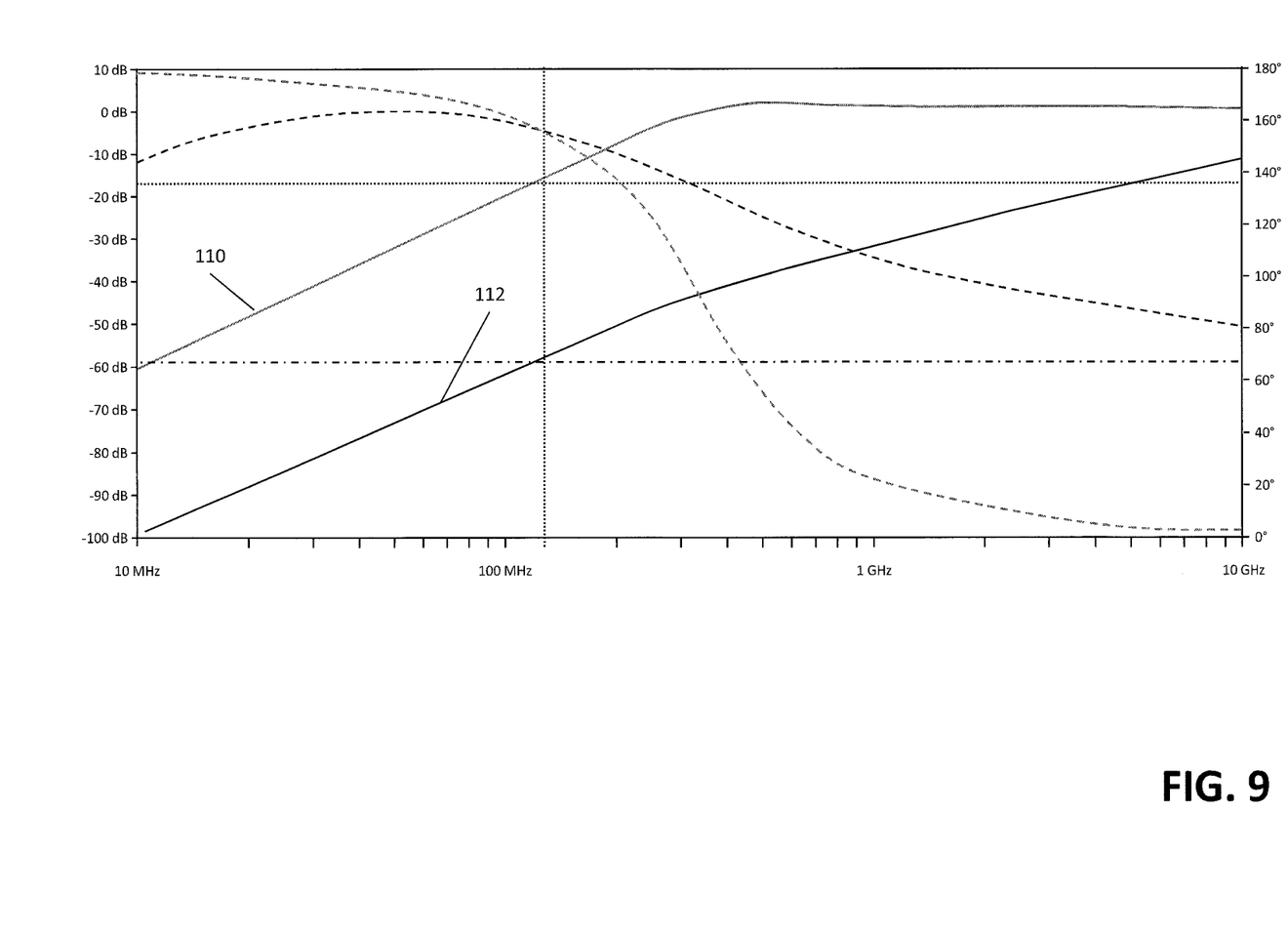
FIG. 9 is a schematic illustration of the attenuation characteristics of the LC high pass filter.

FIG. 9 illustrates a low attenuation level 110 of the exemplary LC high pass filter 100 under normal operating conditions of the dual chamber pacemaker 60, with an unsaturated inductor core 106 respectively. As described in FIG. 5, the inductance of the inductor 104 in such case features a specified value L, which leads to a cutoff frequency $f_c$ of approximately 400 MHz. For frequencies lower than the cutoff frequency $f_c$, the LC high pass filter 100 increasingly attenuates the signal. For a frequency of 200 MHz, as depicted in FIG. 9 with a dotted line, the attenuation amounts to a value of approximately 17 dB.

Furthermore, a high attenuation level 112 of the LC high pass filter 100 is illustrated that applies when the inductor core 106 is saturated. As described in FIG. 5, the inductance of the inductor 104 in such case features a significantly lower value, which leads to a shift of the cutoff frequency $f_c$ to a value of approximately 30 GHz. Through this shift of the attenuation curve towards higher values, the attenuation of the frequencies below the cutoff frequency $f_c$ is in this case significantly lowered compared to the low attenuation level. Particularly, as depicted in FIG. 9 with a dash-dotted line, the attenuation for a frequency of 200 MHz amounts to a value of approximately 60 dB. Such situation is present e.g. when the patient wearing the dual chamber pacemaker 60 is undergoing an MRI examination.

It is also possible to apply the basic concept of the invention, e.g. the intentional use of saturation of an inductor core, to other devices. In particular, this invention can readily be adapted to a number of different kinds of medical devices by following the present teachings, thus rendering the devices MRI compatible. All such changes, modifications and alterations should therefore be recognized as falling within the scope of the present invention.

The invention further includes the recognition that other ways of achieving this object, such as a magnetic sensor together with a switch for disconnecting the antenna from the circuit when an MRI field is present, would imply a significant increase of cost and device complexity, as switching and sensing components had to be added to the device. Also other measures such as applying multistage or higher order filters with additional poles to obtain a sharper cutoff between the frequencies of interest would lead to similar problems as they require additional components and lead to additional attenuation in the radio frequency band. Lastly, the deployment of diode clamps would also require additional components and cost. They would also introduce capacitance into the circuit that would complicate the radio frequency design. Therefore, in contrast to all of these approaches, the application of an LC high pass filter according to the invention achieves the abovementioned object while keeping cost and device complexity low.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. An implantable medical device system comprising an active medical device having or connected to at least one electrode and circuitry connected to the electrode, the system comprising:
   a telemetry unit;
   at least one conductor provided in the circuitry that is connected to the electrode, the at least one conductor providing a radio frequency antenna for the telemetry unit; and
   at least one electronic filter arranged between the at least one conductor and the telemetry unit, the at least one electronic filter comprising at least one inductor having a core or a bead that comprises a ferromagnetic material with saturating behavior when exposed to an external magnetic field.

2. The implantable medical device system according to claim 1, wherein the electronic filter is a high pass filter, a low pass filter or a band pass filter.

3. The implantable medical device system according to claim 1, wherein the electronic filter is arranged and configured to provide low attenuation of electromagnetic fields when the inductor core is not saturated and to provide high attenuation of electromagnetic fields when the inductor core is saturated.

4. The implantable medical device system according to claim 3, wherein the low attenuation is provided for RF magnetic or electromagnetic fields in a first frequency range and wherein the high attenuation is provided for RF magnetic or electromagnetic fields in a second frequency range.

5. The implantable medical device system according to claim 4, wherein the first frequency range has a lower limit of about 400 MHz.

6. The implantable medical device system according to claim 4, wherein the first frequency range encompasses a frequency subrange from 401 MHz to 457 MHz.

7. The implantable medical device system according to claim 4, wherein the second frequency range encompasses at least: a frequency of 128 MHz and/or at least one other frequency associated with the high frequency magnetic field of an MRI machine; or a frequency range from 120 MHz to 136 MHz; or a frequency range from 50 MHz to 150 MHz and/or a frequency range from 60 MHz to 68 MHz.

8. The implantable medical device system according to claim 4, wherein a level of low attenuation of the electronic filter is less than 20 dB and/or a level of high attenuation of the electronic filter is in the range of 20 dB or greater.

9. The implantable medical device system according to claim 1, wherein the electronic filter is a one pole filter or a multi pole filter.

10. The implantable medical device system according to claim 1, wherein the ferromagnetic material is a ferrite or a Mu-metal or a combination of both.

11. The implantable medical device system according to claim 1, wherein the core of the inductor is configured to saturate in a magnetic field with a magnetic flux density that amounts to a value between 1 mT and at least 150 mT.

12. The implantable medical device system according to claim 1, wherein the radio frequency antenna is adapted for wireless communication in a frequency range from 401 MHZ to 457 MHz.

13. The implantable medical device system according to claim 1, wherein the implantable medical device system is connected to an implantable lead, and wherein the electronic filter is arranged at a proximal end of the implantable lead.

14. The implantable medical device system according to claim 13, wherein the implantable lead comprises a lead body and a lead connector, wherein the lead connector is arranged at a proximal end of the lead body, and wherein the electronic filter is arranged within the lead body close to the proximal end of the implantable lead or within the lead connector.

15. The implantable medical device system according to claim 1, wherein the active medical device has an input connected to the electrode, the circuitry connected to the electrode or an implantable lead, wherein the active medical device comprises the telemetry unit, and wherein the electronic filter is arranged between the telemetry unit and the input for the electrode, the circuitry connected to the electrode or the implantable lead.

* * * * *